US008795384B2

(12) United States Patent
Nelson et al.

(10) Patent No.: US 8,795,384 B2
(45) Date of Patent: Aug. 5, 2014

(54) IMPLANTABLE DEVICES USEFUL FOR REINFORCING A SURGICALLY CREATED STOMA

(75) Inventors: Christopher M. Nelson, Lafayette, IN (US); Jessica L. Rose, Holland, OH (US)

(73) Assignee: Cook Biotech Incorporated, West Lafayette, IN ( * ) Notice: Subject to any disclaimer, the term of this patent is extended or adjusted under 35 U.S.C. 154(b) by 1370 days.

(21) Appl. No.: 11/972,274

(22) Filed: Jan. 10, 2008

(65) Prior Publication Data

US 2008/0167729 A1   Jul. 10, 2008

Related U.S. Application Data

(60) Provisional application No. 60/884,258, filed on Jan. 10, 2007.

(51) Int. Cl.
*A61F 2/02* (2006.01)

(52) U.S. Cl.
USPC ...................................... 623/23.72

(58) Field of Classification Search
USPC ........... 606/151, 36; 623/11.11, 23.74, 23.76, 623/23.72; 600/37
See application file for complete search history.

(56) References Cited

U.S. PATENT DOCUMENTS

| 2,127,903 A | 8/1938 | Bowen |
| 2,167,251 A | 7/1939 | Rogers |
| 3,272,204 A | 9/1966 | Artandi et al. |

(Continued)

FOREIGN PATENT DOCUMENTS

| DE | 20318007 | 2/2004 | | |
| WO | WO 2004/071349 | 8/2004 | | |
| WO | WO2004071349 | * 8/2004 | ..................... | 606/151 |
| WO | WO 2007/050382 | 5/2007 | | |

OTHER PUBLICATIONS

International Search Report from PCT/US2008/050744.
Written Opinion from PCT/US2008/050744.

*Primary Examiner* — Gregory Anderson
*Assistant Examiner* — Christina Lauer
(74) *Attorney, Agent, or Firm* — Woodard, Emhardt, Moriarty, McNett & Henry LLP (57) ABSTRACT

An implantable tissue reinforcement device useful for treating or preventing the formation of parastomal hernias forming about a surgically created stoma. The tissue reinforcement device can comprise a synthetic or mammalian-derived sheet-like graft member, such as a resorbable material that promotes tissue ingrowth, wherein a sizing pattern is included that comprises linear indicia radiating outward from a stomal aperture. The linear indicia facilitate creation of a resized stomal opening in the graft member sufficiently large to allow passage of the resected bowel portion. A series of cuts made along the indicia create a plurality of flaps about the resized opening that are configured to abut the bowel portion and enhance reinforcement the stomal region after implantation. In one embodiment, the linear indicia comprises a series of weakened (e.g., perforated) lines that facilitate the cutting of the material by a scalpel, scissors, etc. The clinician resizes the stomal opening to a known diameter using reference indicia, such as diameter indicia and circular guide indicia. The sizing pattern can be imprinted on or etched into the material of the graft member, or it can be at least partially located on a separate template that is either laid over the graft member, preattached as a cuttable overlay, or used as a reference guide.

14 Claims, 4 Drawing Sheets

(56) References Cited

U.S. PATENT DOCUMENTS

| | | | |
|---|---|---|---|
| 3,570,490 A | * | 3/1971 | Berger .................... 604/332 |
| 4,321,914 A | | 3/1982 | Begovac et al. |
| 4,781,176 A | | 11/1988 | Ravo |
| 4,801,299 A | | 1/1989 | Brendel et al. |
| 4,854,316 A | | 8/1989 | Davis |
| 4,902,508 A | | 2/1990 | Badylak et al. |
| 4,956,178 A | | 9/1990 | Badylak et al. |
| 4,969,902 A | | 11/1990 | Ravo |
| 5,269,774 A | | 12/1993 | Gray |
| 5,281,422 A | | 1/1994 | Badylak et al. |
| 5,554,389 A | | 9/1996 | Badylak et al. |
| 5,955,110 A | | 9/1999 | Patel et al. |
| 6,099,567 A | | 8/2000 | Badylak et al. |
| 6,206,931 B1 | | 3/2001 | Cook et al. |
| 6,475,232 B1 | | 11/2002 | Babbs et al. |
| 2003/0026787 A1 | * | 2/2003 | Fearnot et al. .............. 424/93.7 |
| 2005/0288691 A1 | * | 12/2005 | Leiboff ..................... 606/151 |
| 2007/0199836 A1 | * | 8/2007 | Cuomo ..................... 206/162 |
| 2008/0243149 A1 | * | 10/2008 | Kockerling et al. ........ 606/151 |

* cited by examiner

IMPLANTABLE DEVICES USEFUL FOR REINFORCING A SURGICALLY CREATED STOMA

CROSS-REFERENCE TO RELATED APPLICATIONS

This application claims the benefit of U.S. Patent Application Ser. No. 60/884,258 filed Jan. 10, 2007, which is hereby incorporated by reference in its entirety.

TECHNICAL FIELD

This invention relates to medical devices, more particularly to implantable devices useful for body wall repair.

BACKGROUND OF THE INVENTION

An enterostomy procedure, such as a colostomy or illeostomy, is often indicated for patients with colorectal disease or injury to the intestine in which the colon is removed or cannot safely pass solid wastes that would otherwise exit the body through the anus. In such a procedure, the physician must create a stoma, a surgically created opening through the fascia and muscular layers of the lower abdomen, to bypass the compromised bowel section. A bag is typically attached about the stomal opening to collect the patient's feces. In many patients, this a chronic condition so that the stoma and bag remain necessary for the remainder of the patient's life.

A frequent complication of creating an external stoma through the fascia is localized herniation of the bowel through the weakened area around the stomal opening. Without an intact muscle layer maintaining the intestines within the peritoneal cavity, a portion of the bowel may push through or against the weakened area as a visible bulge that is often painful and presents cosmetic issues. In some instances, a loop of the herniated bowel can become strangulated as it pushes out, a potentially serious condition. To correct a hernia problem, the physician is faced with the decision whether to repair the defect or dismantle the original stoma and relocate the opening to the other side of the abdomen, which of course requires a second surgical procedure with its associated morbidity and risks.

Surgical repair of parastomal hernias has been problematic. Resuturing the muscle and supporting tissues adjacent the stoma is a fairly straightforward solution, but long term success rates have been disappointing. Another option has been to implant a synthetic mesh patch around the stoma and suture it in place so that the mechanical load of the bowels against the abdominal wall is spread out over a larger area to reduce the risk of sutures pulling through the muscle, leading to failure of the repair. Mesh devices for parastomal hernia repair are available that include an open 'keyhole' channel extending inward from the lateral edge of mesh implant so that the device can be slipped around the existing stoma and sutured in place, typically beneath the underlying fascia. Preformed flaps about the implant opening extending inward toward the peritoneal cavity help secure the device about the stoma. Implantation of a synthetic mesh parastomal hernia repair device involves wrapping the mesh sheet around the opening and overlapping the edges adjacent the keyhole to 'size' the opening in the mesh to the diameter of the stoma. The mesh is then sutured or stapled to the abdominal wall.

It has been well documented that synthetic hernia repair devices can irritate or erode tissue adjacent the implant over time, which can lead to patient discomfort. Furthermore, synthetic mesh devices are most suitable for repairing an existing hernia and have been recognized as more problematic as a prophylaxis implant because concerns with field contamination and other complications. Given the high incidence of hernia formation around the stomal opening in patients having an ostomy procedure, it has been proposed that prophylactic reinforcement of the site around the surgically created stoma would be warranted as a means to reduce the incidence of post-surgery hernias.

What is needed is a hernia repair device configured to be safely and securely implanted about the region of the surgically created stoma and which can be configured according to patient anatomy to provide long term reinforcement of the stomal site, either prophylactically or to repair an existing hernia, without the complications and hernia recurrence rates associated with permanently-implanted synthetic mesh devices.

SUMMARY OF THE INVENTION

The foregoing problems are solved and a technical advance is achieved in an illustrative implantable device for reinforcing tissue surrounding a surgically created stoma in a patient. Accordingly, in one embodiment of the invention, a tissue reinforcement device comprises a graft member comprising one or more layers of a naturally-derived (e.g. collagenous) or synthetic biocompatible material, such as a bioremodelable or bioactive extracellular matrix (ECM) material, that is effective to reinforce the area generally surrounding the surgically created stoma, such as to repair a herniation of the intestines through or around the stoma, or to reinforce the stomal region prophylactically at the creation of the stoma to prevent a hernia. The material of the graft member may remain as a permanent implant material in the host tissue or more preferably, the material of the graft member is resorbable by the body during or after the generation of a new bed of reinforcing tissue around the stomal site. The graft member includes a stomal aperture located within the central portion thereof, that is configured to be conveniently adjustable in size according to the diameter of the surgically created stoma. To aid in the resizing of the aperture by the clinician, a sizing pattern is applied to the surface of the graft by imprinting, etching, burning, or otherwise marking the material directly, or by the addition of a separate element comprising at least a portion of the sizing pattern, such as a template that is laid over the material, used as a reference, or physically attached thereto (e.g., an overlay). The sizing pattern conveniently provides a visual guide to the clinician in the creation of the appropriate resized stomal opening and flaps that encircle the opening.

In another aspect of the invention, the sizing pattern comprises a plurality of linear indicia that extend radially outward from the aperture of the graft member or template to visually guide the clinician as the cuts in the material are made during the creation of the flaps. The linear indicia may advantageously comprise weakened lines in which graft material is partially removed (e.g., perforated) or otherwise weakened structurally (e.g., scoring) to facilitate cutting there along with scissors, scalpel, etc., to create the flaps while enlarging the opening.

In still another aspect of the invention, the sizing pattern comprises a series of indicia that facilitate the resizing of the stomal aperture by identifying the diameter at a given point along the linear indicia to which the cuts should be made to achieve the desired resized stomal opening. In one embodiment, the linear indicia comprise a series of perforations formed through the material or other visible markings at regular spaced intervals, the individual perforations or other markings corresponding to a reference diameter that is identified on the surface of the graft material or on an overlying template as numerical value. Additionally, each of series of concentric circular guides of increasing diameter intersect the perforations at a particular reference diameter, while cut line indicia extending through the perforations along the weakened lines in the material provide a further means to visually identify where the cuts should be made to resize the stomal aperture and form the flaps.

In yet another aspect of the invention, the graft includes a stomal aperture access pathway extending between the aperture and a lateral edge of the material that may comprise either an open channel that allows the graft to be positioned around the surgically created stoma for implantation, or a closed pathway that is typically aligned with one of the linear indicia. The closed stomal aperture access pathway is adapted for being conveniently reconfigured to an open pathway, such as by including a weakened line (e.g., perforations) there along. Leaving the stomal aperture pathway at least partially closed advantageously provides the option of implanting the graft prophylactically prior to creation of the stoma so that an open channel, which would represent an unnecessary weak area, would not be present as a potential source of graft failure.

Still yet another aspect of the invention is a method for implanting a graft to reinforce the area around a surgically created stoma, the method including the steps of providing a graft member of the present invention, determining a desired diameter of the resized stomal opening (e.g., one that corresponds with the diameter of the resected bowel portion extending through the stoma), visually referencing the sizing pattern during enlargement of the stomal aperture with a cutting instrument to the desired diameter, then implanting the graft member about the surgically created stoma so that the flaps created about the resized stomal opening of the graft member abut the resected bowel portion as it extends therethrough. In one method, the stomal aperture access pathway is open or opened prior to implantation so that the graft member with the resized stomal opening is placed around the preexisting stoma and affixed to the adjacent peritoneal wall or fascia of the patient, such as by suturing or a surgical bonding technique. In another method, the stomal access pathway remains closed (no open channel or slot extending from the stomal aperture to the edge of the graft member). The graft member can then be implanted in a fashion wherein the resected bowel is passed through the resized stomal opening in the graft, for example prophylactically implanted prior to creation of the stoma so that the resected bowel portion can be drawn through the resized stomal opening of the graft member without unnecessarily weakening the material along that pathway.

Additional embodiments as well as features and advantages of the invention will be apparent from the further descriptions herein.

BRIEF DESCRIPTION OF THE DRAWINGS

Embodiments of the present invention will now be described by way of example with reference to the accompanying drawings, in which.

DETAILED DESCRIPTION

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, $27^{th}$ edition. It is therefore intended that the foregoing detailed description be regarded as illustrative rather than limiting, and that it be understood that it is the following claims, including all equivalents, that are intended to define the spirit and scope of this invention.

In certain aspects, the present invention, as illustratively embodied in FIGS. 1-8, relates to an implantable tissue reinforcement device 10 that includes a graft member 11 comprising a resorbable material, such as a remodelable sheet material derived intact from a mammalian tissue source and processed to an acellular form. The graft member 11 further includes a stomal aperture 12 located about the central portion 19 of the graft member 11 (not necessarily at the center) through which a resected portion of the bowel 34 is drawn therethrough to create a surgically created stoma 37 that extends through the abdominal wall of the patient, the stomal aperture typically being intentionally undersized with respect to the general diameter of the surgically created stoma 37. To facilitate resizing the aperture 12 to allow for passage of the bowel 34 therethrough, the device 10 further includes a sizing pattern 13 that provides a visible guide to the clinician to allow enlarging the stomal aperture 12 to a known diameter in accordance to the patient's anatomy and in the process, create a plurality of flaps 21 about the enlarged stomal opening 40 (e.g., FIG. 8) that abut the bowel as it traverses therethrough.

Figure 1:
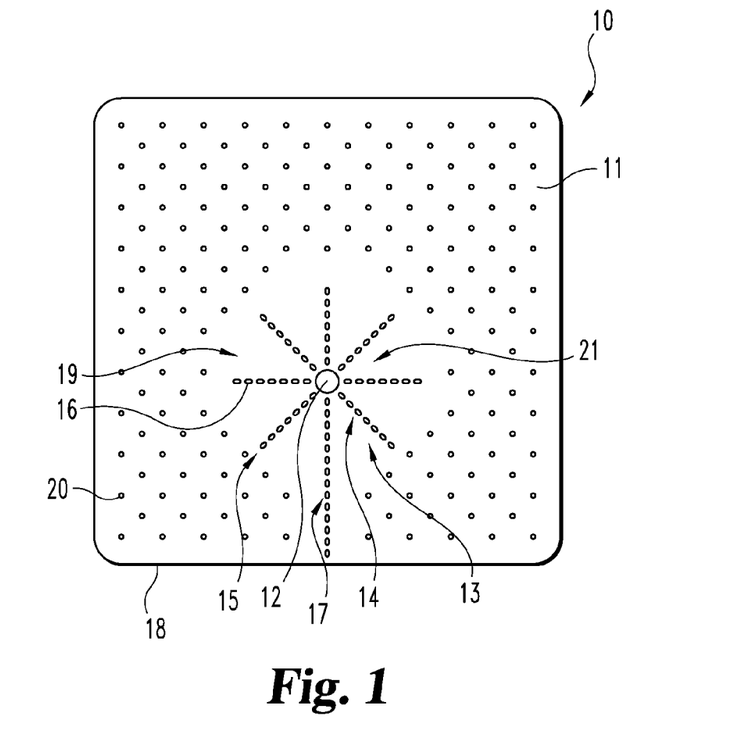
FIG. 1 depicts a top view of the illustrative embodiment of the present invention.

Now referring to FIG. 1, the illustrative tissue reinforcement device comprises a graft member 11 comprising an ECM material, preferably a multilaminate ECM material such as SurgiSIS™ ES (Cook Biotech, Inc., West Lafayette, Ind.), which is a multilaminate construct formed of a plurality of intact sheets of ECM material that comprise porcine small intestinal submucosa (SIS) that are hydrated, laid on top of one another according to the desired thickness and strength, then the sheets are frozen in a −80° C. freezer for at least 2 hours, then vacuum dried to create a lyophilized multilaminate construct. Illustrative processes for creating a lyophilized multilaminate materials are taught in U.S. Pat. No. 6,666,892 to Hiles et al. which is expressly incorporated by reference herein. The number of sheets comprised of SIS used to form the graft member 11 of the present invention that is effective as a reinforcement to prevent reherniation around the surgically created stoma may range from 3 to 10, with a more preferable range of 4-6, most preferably six. Alternatively, the graft member can comprise a plurality of SIS- or other ECM-containing sheets that are vacuum pressed to form a multilaminate tissue reinforcement device 10 (similar to SURGISIS™ GOLD, Cook Biotech, Incorporated), one general method of manufacture being taught in U.S. Pat. No. 5,711,696 to Patel et al., which is expressly incorporated by reference herein. Other methods of producing a graft member 11 of sufficient strength to function for the intended purpose should be within the ability of one of ordinary skill in the tissue engineering arts. As a means to facilitate the passage of fluids through the implanted graft member and mitigate seromal fluid buildup at the implantation site, which could have a negative impact on the ability of the graft material to remodel, the graft member can include a plurality of drainage apertures 20 distributed over the graft member 11, preferably, but not necessarily, spaced away from the stomal aperture 12 and the area comprising the flaps 21. A method for forming perforated material is taught in U.S. Pat. No. 5,755,791 to Whitson et al., which is expressly incorporated by reference herein.

Materials comprising submucosal tissue such as SIS represent a particularly advantageous choices of materials for the present tissue reinforcing device 10 because of their capacity to be processed to have strength (particularly as a multilaminate construct) and bioactivity, which allows them to be gradually replaced by an ingrowth of new cells, capillaries, etc., as the implanted collagenous matrix is resorbed by the body, such that the remodeled tissue is of sufficient strength to reinforce the implantation site such that herniation or reherniation is unlikely to occur. Bioresorbable materials provide advantage in the present invention, with materials that are bioremodelable and promote cellular invasion and ingrowth (and angiogenesis) providing particular advantage. In contrast, non-resorbable polymer meshes rely on the continued strength and durability of the synthetic material to maintain reinforcement of the stomal site and prevention of reherniation, rather than promoting the establishment of the patient's own tissue to reinforce the weak area around the stoma. Furthermore, patients often have complained that they can feel the mesh as it irritates the tissue around the implant site, sometimes requiring further surgical intervention. Nonetheless, in alternative embodiments, non-resorbable polymer meshes or other non-resorbable materials can be used in the graft devices of the invention.

Resorbable graft materials further having advantage as being bioremodelable and capable of promoting new tissue ingrowth include collagenous extracellular matrix materials (ECMs) that possess biotropic properties. For example, suitable collagenous materials include ECMs such as submucosa, renal capsule membrane, dermal collagen, dura mater, pericardium, serosa, peritoneum or basement membrane layers, including liver basement membrane. Suitable submucosal materials for these purposes include, for instance, intestinal submucosa (e.g., small intestinal submucosa), stomach submucosa, urinary bladder submucosa, and uterine submucosa. It will be understood that submucosal tissue materials isolated from these or other sources can optionally include material from adjacent tissue layers, such as lamina propria, stratum compactum, basement membrane or other materials.

As prepared and used, the submucosal material and any other ECM used, may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosal or other ECM material may include a bioactive component that induces, directly or indirectly, a cellular response such as a change in cell morphology, proliferation, growth, protein or gene expression.

Further, in addition or as an alternative to the inclusion of such native bioactive components, non-native bioactive components such as those synthetically produced by recombinant technology or other methods, may be incorporated into the submucosa tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the occlusion devices include, for example, analgesics, antibiotics, thrombus-promoting substances such as blood clotting factors, e.g. thrombin, fibrinogen, and the like. These substances may be applied to the occlusion device as a premanufactured step, immediately prior to the procedure (e.g. by soaking the material in a solution containing a suitable antibiotic such as cefazolin), or during or after deployment of the occlusion device in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention. Additionally, the submucosa or other ECM tissue may be prepared as, and may have the characteristics of, the material as described in U.S. Patent Application Ser. No. 60/853,584 filed Oct. 23, 2006 and/or International Patent Application No. PCT/US2007/82238, both entitled PROCESSED ECM MATERIALS WITH ENHANCED COMPONENT PROFILES, which are hereby incorporated herein by reference in their entirety. Accordingly, in certain embodiments, the ECM material retains collagen and non-collagen components, and desirably exhibits an angiogenic character. At the same time, the submucosa-containing or other ECM material has low levels of undesired components such as native lipids, nucleic acids (e.g. DNA), and/or immunoglobulin A (IgA) components. In some embodiments, the ECM can be a sterile, decellularized extracellular matrix (ECM) material including native fibroblast growth factor-2 (FGF-2), and native immunoglobulin A (IgA) at a level of no greater than 20 µg/g. In some forms, this ECM material can have a lipid content of no greater than about 4%. In still further aspects, the ECM material can have a native FGF-2 content of at least about 10 ng/g and at least one of, and in certain forms each of (i) native IgA at a level of no greater than about 20 µg/g; (ii) native lipids at a level of no greater than about 4% by weight; (iii); (iv) native hyaluronic acid at a level of at least about 50 µg/g; and (v) native sulfated glycosaminoglycan at a level of at least about 500 µg/g. These unique ECM materials can be prepared by processing methods that comprise treating a relatively impure ECM starting material to decrease the content of the undesired components, such as nucleic acid, lipids and/or immunoglobulins such as IgA, while retaining substantial levels of desired components such as growth factor(s), proteoglycans and/or glycosaminoglycans (GAGs). Typically, to prepare such preferred ECM materials, an ECM starting material will be treated with a mild detergent solution, such as an ionic or nonionic detergent solution. The low concentration of detergent enables a retention of a substantial level of desired components, such as those as noted above. In certain modes of operation, the ECM material will be treated with an aqueous solution of sodium dodecyl sulfate (SDS) or another ionic or nonionic detergent at a detergent concentration of about 0.05% to about 1%, more preferably about 0.05% to about 0.3%. This treatment can be for a period of time effective to disrupt cell and nuclear membranes and to reduce the immunoglobulin (e.g. IgA) content of the ECM material, typically in the range of about 0.1 hour to about 10 hours, more typically in the range of about 0.5 hours to about 2 hours. Processing the isolated ECM material in this manner preferably disrupts cell and nuclear membranes and results in a material with a substantially reduced its IgA content, thus reducing the immunogenicity of the material. In addition to treating an ECM material with a detergent medium, the ECM material can be contacted with other agents that participate in achieving the desired ECM component profile. For example, the ECM material can be treated with an aqueous medium, preferably basic, in which DNA is soluble. Such a medium can in certain forms have a pH in the range of above 7 to about 9, with pH's in the range of about 8 to about 8.5 proving particularly beneficial in some embodiments. The basic aqueous medium can include a buffer, desirably a biocompatible buffer such as tris(hydroxymethyl)aminomethane (TRIS), and/or a chelating agent such as ethylene diamine tetraacetic acid (EDTA). In one preferred form, the nucleic acid solubilizing medium is a TRIS-borate-EDTA (TBE) buffer solution. This treatment with a DNA solubilizing medium can be for a period of time effective to reduce the DNA content of the ECM material, typically in the range of about 0.1 hour to about 10 hours, more typically in the range of about 0.5 hours to about 2 hours. In addition to treatment with detergent and DNA-solubilization media, methods of preparing medical graft materials of the invention can involve treatment with a liquid medium that results in a substantial reduction of the level of lipid components of the ECM material. For example, the resulting native lipid content of the ECM material can be reduced to no greater than about 4% in certain embodiments. This can be accomplished, for example, by a preparative process that involves a step of treating the ECM material with a liquid organic solvent in which the lipids are soluble. Suitable such organic solvents include for example water-miscible solvents, including polar organic solvents. These include low molecular weight (e.g. C1 to C4) alcohols, e.g. methanol, ethanol, isopropanol, and butanols, acetone, chloroform, and others. This treatment with a lipid-removing medium can be for a period of time effective to reduce the lipid content of the ECM material, typically in the range of about 0.1 hour to about 10 hours, more typically in the range of about 0.1 hours to about 1 hours. In certain embodiments, multiple (two or more) such treatments will be conducted.

In addition to the aforementioned naturally derived biomaterials, bioresorbable polymeric and other synthetic matrices are contemplated as a graft member material. Researchers in the field of regenerative medicine have developed a number of synthetic matrices, typically comprising a web or fabric of resorbable polymer strands or cast layer engineered to serve as a substrate for the propagation of seeded cells or those ingrowing from adjacent tissues. Growth factors and other signaling molecules, including but not limited to those identified herein, can also be added to the synthetic matrix to encourage cells ingrowth. It is also within the scope of the invention for the graft member material to comprise materials that are substantially non-resorbable by the body and persist in some form, typically after being encapsulated by host tissue. Examples include traditional durable polymers used in body wall repair, such as polypropylene or polytetrafluoroethylene, as well as collagenous materials that are cross-linked so that they resist degradation after implantation in the body.

Figure 2:
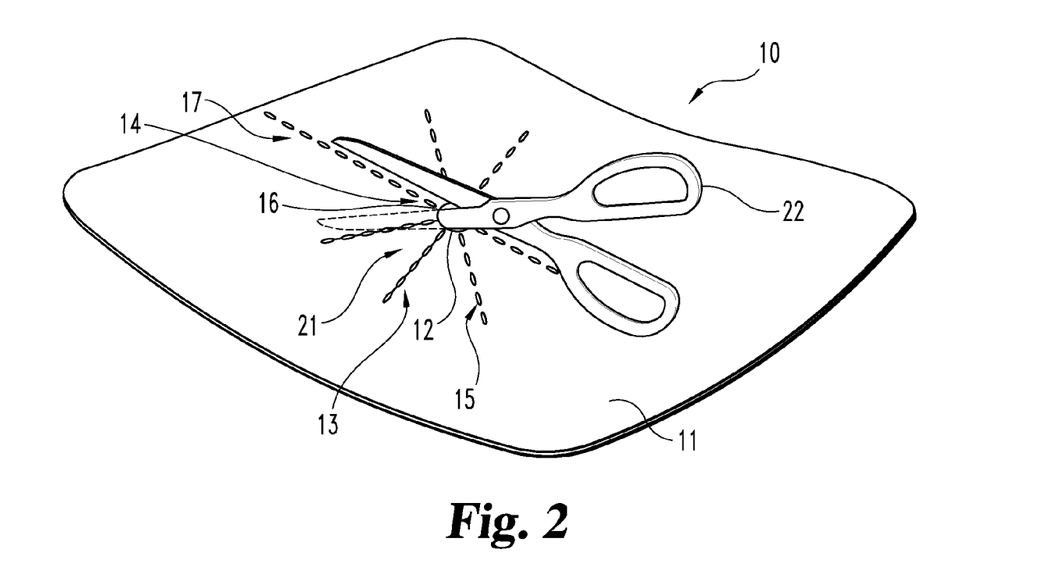
FIG. 2 depicts a perspective view of the embodiment of FIG. 1 being resized.

Now referring to both FIGS. 1 and 2, the illustrated tissue reinforcement device of the present invention depicted includes a tissue sizing pattern 13 that comprises a series of linear indicia 14 to guide the clinician in creating a series of flaps 21 using a cutting instrument 22, such as a pair of scissors, scalpel, etc. (FIG. 2). In the illustrative embodiment, the linear indicia 14, which identify where the clinician should cut through the graft material to form the flaps 21, comprise a plurality of weakened lines 15 configured to facilitate the traversal of the tough laminated graft material with the cutting instrument. Each weakened line 15 comprises a series of perforations, about 1 mm wide and 3 mm in length, that are separated from one another at regular intervals (e.g., 1-2 mm) of intact graft material. The perforations can comprise any suitable configuration and may be identical or unique from one another (such as to identify relevant points for determining sizing). For example, the material can be cut away so that the perforations comprise numerals, different shapes, or clusters of varying number of holes, etc. Additionally, the perforations or other linear indicia can have any suitable linear configuration, including straight (e.g. spoke-like) or curved linear paths.

Figures 6, 7:
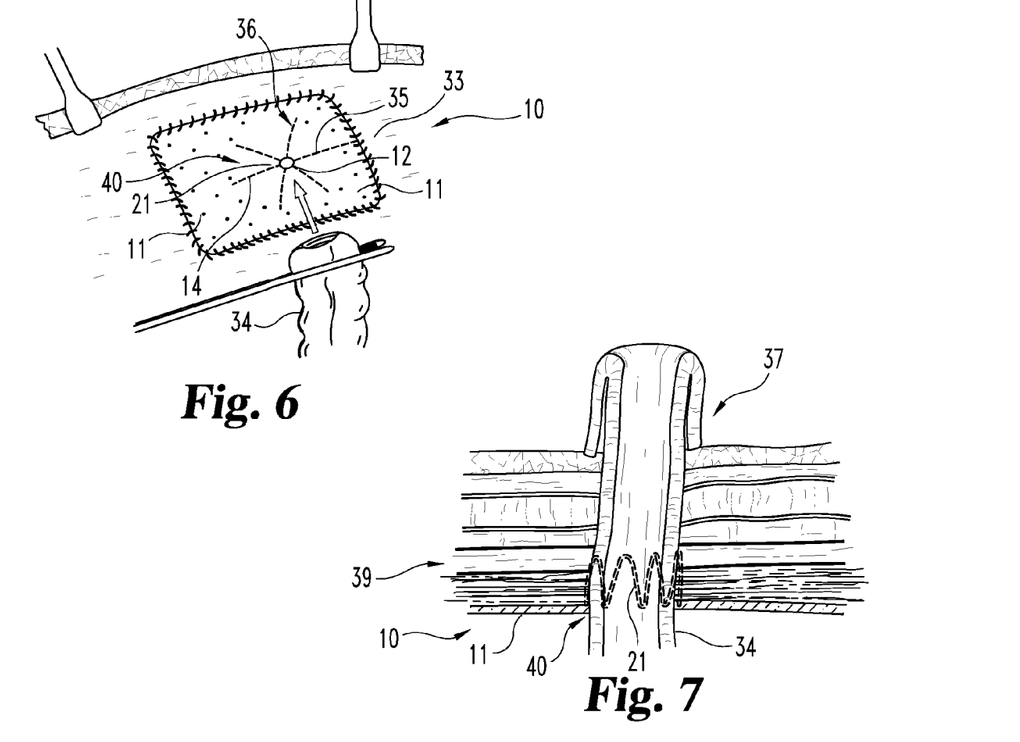
FIGS. 6-8 depict in vivo views of methods of implanting the embodiment of FIG. 1.
Figure 8:
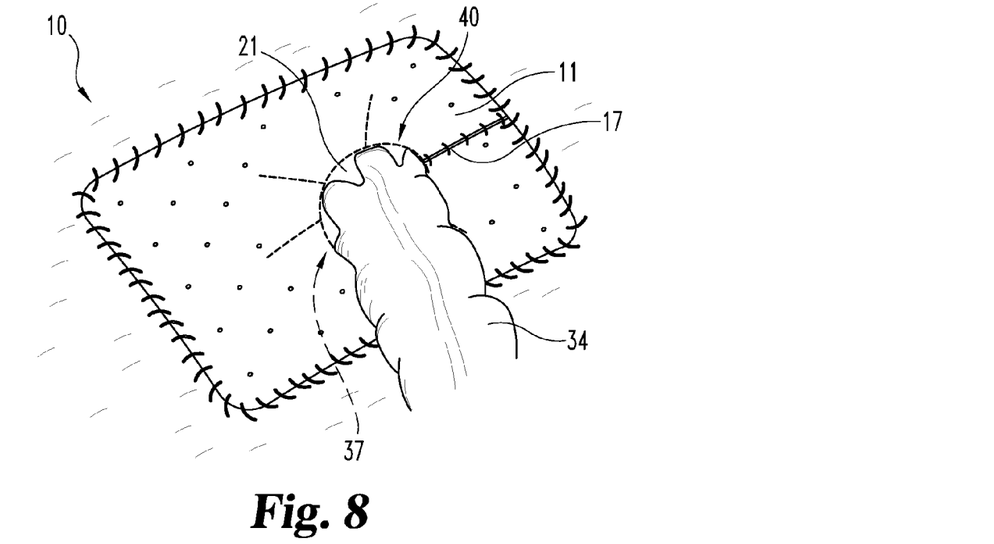

In one method forming the flaps and resizing the stomal aperture, the clinician inserts the cutting instrument into the stomal aperture 12 of the graft member 11 and begins cutting through the material in an outward direction until reaching the desired diameter of the resized stomal opening 40 (depicted in FIGS. 6-8). This step is then repeated along each of the weakened lines 15, thereby creating the plurality of flaps 21 as the stomal aperture 12 is resized. The resized stomal opening 40 comprises a diameter that generally corresponds to the diameter of the resected bowel portion that is then drawn through the stomal aperture to create the surgically created stoma on the lower abdomen of the patient. In the illustrative embodiment (e.g., FIG. 1), the sizing pattern 13 comprises eight weakened lines 15 such that eight flaps 21 are created about the resized stomal aperture 12, however fewer or more lines and flaps are also contemplated (e.g., 3-12, more preferably 6-8).

As depicted in the embodiment of FIG. 1, one of the linear indicia 14 comprises a weakened line 15 that extends toward the edge 18 of the graft member 11 to form a stomal aperture access pathway 17. If lateral access to the stomal aperture is desired, such as when the clinician is placing the graft member around an existing stoma to reinforce an area through which a herniation has already occurred, the stomal aperture access pathway 17 is traversed from the stomal aperture 12 to the edge (from either direction) prior to implantation to create an open channel or slot (sometimes called a 'keyhole') that allows the clinician to wrap the graft member 11 around the bowel portion and suture or otherwise affix the graft member in place. If the graft member 11 is to be placed prophylactically before the surgically created stoma is created, to lower the risk of a post-implant herniation occurring, the physician typically would not cut all the way to edge along the stomal aperture access pathway 17, rather only from the stomal aperture 12 outward to the desired diameter in the same manner as the other linear indicia 14 (FIG. 2), since the resected bowel can be drawn through the opening, as discussed later in this application, and the portion of the graft member that includes the stomal aperture access pathway is not unnecessarily weakened. Of course, it is within the scope of the invention for the tissue reinforcement device 10 to be manufactured such that the stomal aperture access pathway 17 comprises an open channel.

The sizing pattern of FIG. 1 is configured to both provide a template for the creation of the plurality of flaps that engage the stoma, as well as to provide a dimensional guide to assist the clinician in resizing the stomal aperture 12 to the appropriate desired diameter. In the illustrative embodiment, the perforations 16 comprising the weakened lines 15 are spaced at known distance intervals from the stomal aperture 12 such that by cutting the graft material outward along the linear indicia lines 14 to a particular perforation that corresponds to a known diameter, the clinician can enlarge the stomal aperture of the graft member 11 to that desired diameter. For example, the illustrative perforations are radially spaced 1 cm apart such that when the clinician cuts along the weakened line 15 into the first perforation 16 extending from the stomal aperture 12 (FIG. 2), and repeated along each of the weakened lines, the stomal aperture is enlarged from 1 cm to 2 cm. If the desired size of the stomal aperture 12 is 3 cm, the clinician cuts along the weakened lines into the second level of perforations, and so forth. These and other arrangements wherein the perforations or other indicia of the sizing pattern provide a scale to be employed by the user are contemplated as being within the present invention.

Figure 3:
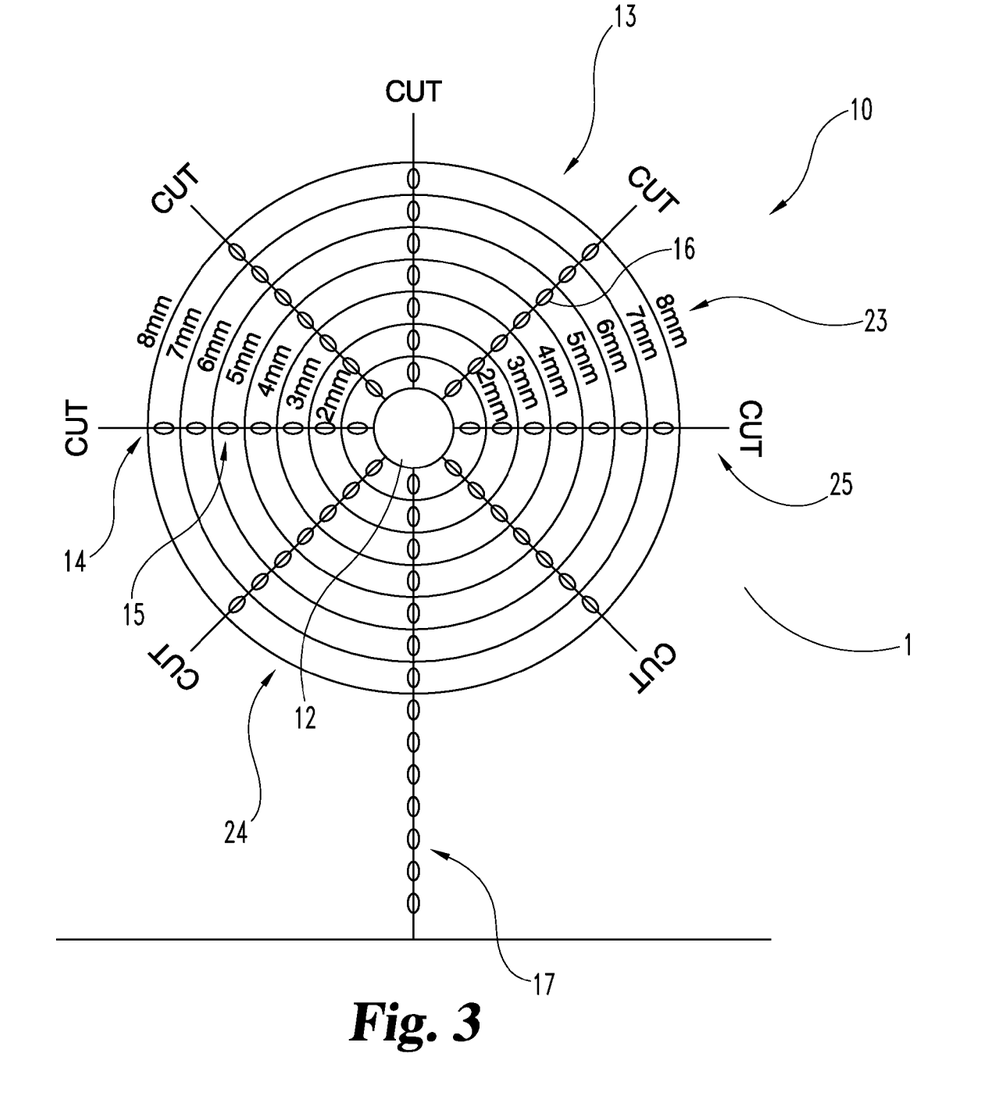
FIG. 3 depicts a top view of an embodiment of the present invention with an alternative sizing pattern.

FIG. 3 depicts a graft member 11 in which the sizing pattern 13 includes various reference indicia that are added to the material comprising the graft member by a method such as laser or chemical etching, mechanical abrasion, etc. to remove a layer of material or by applying the indicia using a biocompatible ink, dye, or other material that can be imprinted or embossed onto the surface of the graft member surface. In the illustrative embodiment, the sizing pattern 13 comprises (in addition to the eight linear indicia 14 or weakened lines 15) a series of diameter indicia 23 that identify the particular level of perforations 16 that would produce a resized stomal aperture 12 of that diameter (2 cm-8 cm), preferably using the actual numerical value identifying the diameter, although other unique indicia may be used instead for each level. The different levels or resize diameters include circular guide indicia 24, comprising a series of concentric circular lines that interconnect the eight perforations 16 that lie at a particular diameter, which is indicated by the diameter indicia 23. The sizing pattern further includes cut line indicia 25 that comprise a series of visible lines that extend through the perforations 16 along a particular weakened line 15, as well as an optional instructional indicator 'CUT' which is positioned at the terminus of the visible line, which extends beyond the most distant perforation.

As an alternative means of providing a sizing pattern 13 that includes the appropriate metrics and other visible guides, the sizing pattern may be imprinted on a overlay (not shown) comprising a transparent, translucent, or opaque material, such as polymer film, cellulose, paper, fabric, etc., or incorporated into the overlay by some other appropriate technique (e.g., a physical alteration or removal of the material). The overlay, which is a form of template (other examples discussed below), can be placed over the graft member 11 or lightly bonded to its surface, such as by a weak adhesive or physically attached by some other means, such as temporary sutures. It is configured so that the clinician can readily cut through the overlay and graft member simultaneously along the linear indicia 14, using the numerical diameter indicia 23 to determine how much of the line should be cut to produce the desired resized stomal aperture 12. For example, the overlay could include the numerical diameter indicia 23 and other guides such as the circular guide indicia 24 and cut line indicia 25 depicted in FIG. 3, while being affixed to the graft member of FIG. 1, which includes the weakened lines 15 that would correspond to the cut line indicia 25 on the overlay, when the overlay is properly aligned on the graft member. When the flaps 21 have been cut and the stomal aperture 12 resized, the overlay is then peeled off or otherwise removed and discarded.

Figure 4:
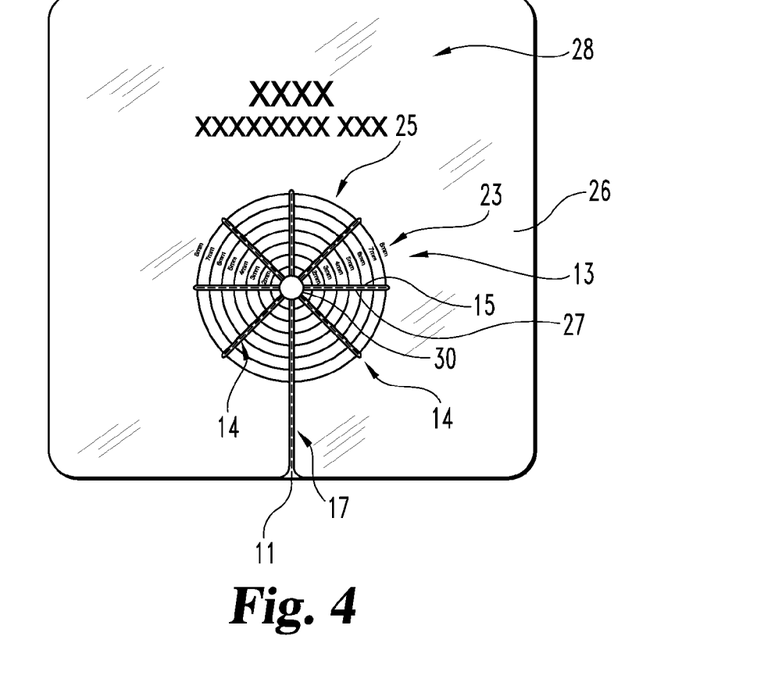
FIGS. 4-5 depict top views of templates of the present invention comprising sizing patterns.
Figure 5:
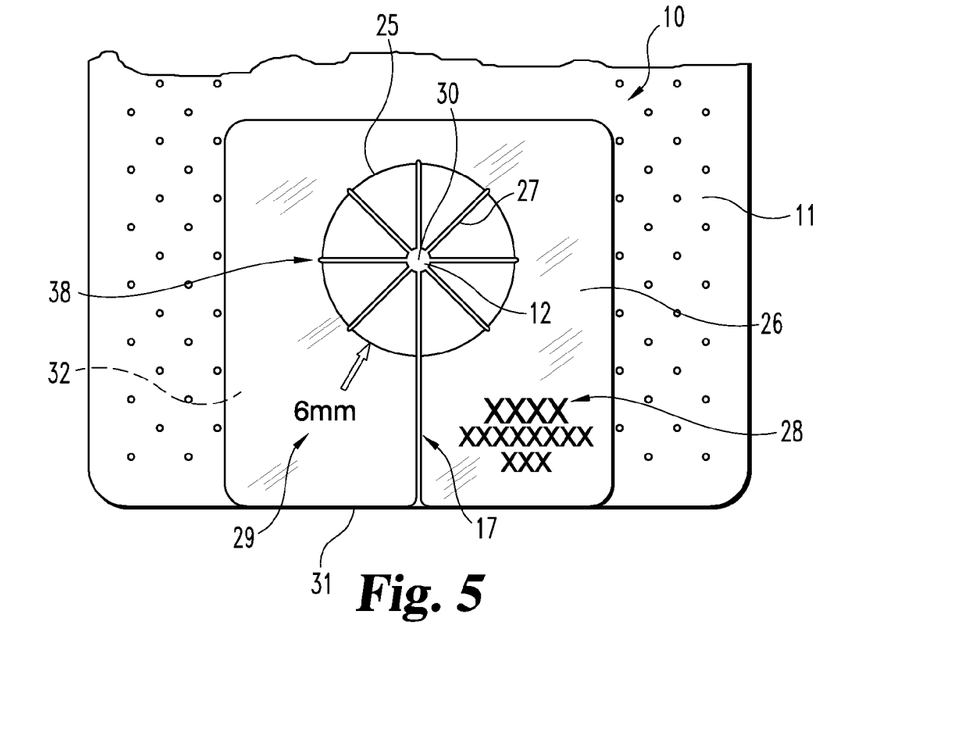

FIGS. 4-5 depict embodiments in which at least the portion of the sizing pattern 13 that allows the clinician to resize the stomal aperture to the optimal diameter is located on a separate template that is temporarily laid over the graft member to identify the length of the cut required to produce the desired stomal opening size. In the illustrative embodiment of FIG. 4, the template 26 comprises a durable material, such a stainless steel or hard plastic, that includes a pattern of open slots 27 that extend from a template opening 30 in the template such that when the template is properly aligned by superimposing it over the graft member 11, the template opening corresponds to stomal aperture 12 thereof. The numerical diameter indicia 23 and circular guide indicia 24 are imprinted, etched, etc., on the surface of the template to guide the clinician as the cutting instrument is used to traverse the graft material within the open slot to the appropriate circular guide/diameter. The open slots 27 may correspond to weakened lines 15 in the graft member (linear indicia 14) that facilitate cutting and/or provide a further means of identifying the appropriate diameter, or the slots may align with etched or imprinted linear indicia located on the graft member 11. Alternatively, the graft member may lack any markings or weakened lines such that the linear indicia 14 for guiding the creation of the flaps are located only on the template 26. In another embodiment, the template can comprise a reference card, transparent guide, etc. that includes the diameter indicia 23, whereby the template is not laid over the graft during the process of making the desired cuts for resizing, but rather used as a visual guide comprising at least part of the sizing pattern to help the clinician determine the particular perforation or point along the linear indicia to which the cut should extend, whereby the template is set aside while the cut is made.

In an alternative embodiment depicted in FIG. 5, separate templates 26 are created for each diameter such that by extending the cuts outward from the stomal aperture 12 to the distal end 38 of each slot 27 in the template, the stomal aperture is resized to the designated diameter unique to that particular template 26. For example, the illustrative embodiment is configured to produce a resized stomal opening diameter of 6 cm, while a different template would be selected to produce a different-sized stomal opening (2, 3, 4, 5, 7 or 8 cm). The slot 27 corresponding to the stomal aperture access pathway 17 extends to the template's outer edge 31 so to permit cutting the graft member 11 to its outer edge 18 when the reinforcement device 10 is used to repair an existing hernia. Thus, a circular guide 24 located on the template 26 advantageously assists the clinician in making an appropriate-length partial cut along that slot 27 when the device is to implanted prophylactically prior to creation of the stoma.

The templates 26 of FIGS. 4 and 5 can be packaged with the graft member 11 for single use or they may be provided as reusable components, particularly if made of stainless steel or other material suitable for resterilization. Metal advantageously allows the template to be used with the cutting instrument so that if the sides of the slot 27 are accidentally nicked or contacted during the cutting procedure, there is much less risk of unwanted shavings of template material being left on the graft member and introduced into the patient. Harder plastics may be appropriate as well if care is taken to avoid slicing away material, or metal can be used in combination with plastic to provide protection along the insides of the slots. Particularly when a template might be reused, it is advantageous to include device information 28 to identify the template that is appropriately sized or configured to be used with a particular graft member 11, as depicted in FIGS. 4-5. The device information might include the company name, model number/graft configuration, and/or contact information for obtaining technical information, reordering, etc. Additionally, the embodiment of FIG. 5 would include the particular size identification 29 unique to that particular member of the series of templates 26.

FIGS. 6-8 depict selected options for placement of the tissue reinforcement device within the patient. FIG. 6 depicts a graft member 11 of FIG. 1 that has been placed prophylactically to provide reinforcement to the area stomal opening prior to its creation. After the stomal aperture has been resized to a larger opening 40 according to the diameter of the resected bowel, the graft member 11 is sutured or otherwise surgically attached or bonded to the wall of the peritoneum 33 adjacent the site on the lower abdomen where the surgically created stoma is to be located (some physicians may elect to resect the peritoneum and attach the graft material to the fascia). To create the surgically created stoma, an incision is made through the abdominal wall and the resected end of the healthy portion of the bowel 34 is pushed through the resized stomal opening 40 and fascia where it is sutured in place to create the surgically created stoma 37 (FIG. 7). The stoma is typically connected to an external collection device, such as an ostomy bag, so that the damaged or diseased portion of the intestines can be bypassed. As depicted in FIG. 7, the flaps 21 may be drawn upward through the fascia 39 in the process, whereby they may advantageously remodel into native tissue to help reinforce the that region of the surgical stoma 37 which is particularly vulnerable to hernia formation. Depending on physician preference, the flaps 21 may instead be redirected downward (during or after implantation of the graft) so that they would appear similar the example in FIG. 8, which shows a placement of a graft member 11 when being used to repair an existing parastomal hernia. In this procedure, the surgically created stoma is already in place with the resected bowel portion extending outward through the abdominal wall. Thus, graft member 11 is configured or reconfigured such that the stomal aperture access pathway 17 comprises an open channel or keyhole so that the graft member 11 can be placed around the bowel and stoma, then sutured or otherwise attached to the peritoneum after the stomal opening 40 has been resized appropriately. The stomal aperture access pathway 17 can be opened for lateral access using a cutting instrument just prior to implantation or the slot may be preformed during manufacture of the device, like commercially available synthetic devices. Typically, the flaps 21 created when resizing the stomal aperture are oriented downward when the graft member 11 is implanted at the stomal site, although they may be manually redirected into the fascia once the graft member 11 is secured in place. It will be understood, however, that other arrangements for the flaps 21 are also possible. For example, in the implanted configuration, the flaps may be oriented either downward (away from the skin) or upward (toward the skin) or both (e.g. with alternating flaps in the downward and upward direction). Further, in any or all of these configurations, the securement of the flaps can be reinforced with a cuff or completely or partially wrapped piece of reinforcement material, such as an additional amount of the material from which the graft member is made (ECM or otherwise), which covers and reinforces the flaps against the associated length of bowel.

What is claimed is:

1. An implantable device for reinforcing tissue surrounding a surgically created stoma in a patient, the device comprising:
   a graft member comprising one or more layers of a biocompatible material effective to provide reinforcement of an area generally surrounding a surgically created stoma when implanted thereabout;
   a stomal aperture disposed within a central portion of the graft;
   a sizing pattern on the graft member comprising a plurality of weakened lines extending radially from the stomal aperture such that when the stomal aperture is enlarged by separation of the biocompatible material along paths defined by the weakened lines, a plurality of flaps is created about the enlarged stomal opening; and
   the biocompatible material being cuttable to any of a plurality of locations along the weakened lines to form any of a plurality of corresponding modified graft members having an enlarged stomal opening, with said modified graft members each being effective to provide reinforcement of an area generally surrounding a surgically created stoma so as to resist herniation or reherniation around the stoma.

2. The tissue-reinforcement device of claim 1, wherein the sizing pattern further comprises a series of diameter indicia disposed at regular intervals there along that identify the diameter of a particular resized stomal opening created of the particular diameter.

3. The tissue-reinforcement device of claim 1, wherein said plurality of weakened lines comprises a series of perforations formed in the graft material at regular intervals.

4. The tissue-reinforcement device of claim 3, wherein the sizing pattern comprises a series of concentric circular guides located at regular intervals from the stomal aperture.

5. The tissue-reinforcement device of claim 1 wherein the biocompatible material comprises one or more sheets of tissue that have been decellularized.

6. The tissue-reinforcement device of claim 1, wherein the biocompatible material comprises one or more intact sheets of tissue processed to an acellular form.

7. The tissue-reinforcement device of claim 1, wherein the graft comprises a stomal aperture access pathway extending from the stomal aperture outward to an outer edge of the graft.

8. The tissue-reinforcement device of claim 7, wherein the stomal aperture access pathway comprises one of an open channel or slit formed in the graft material.

9. The tissue-reinforcement device of claim 7, wherein the stomal aperture access pathway comprises a weakened line configured to facilitate creation of an open channel or slit through the graft material.

10. The tissue-reinforcement device of claim 1, wherein the graft member material is effective to stimulate ingrowth of reinforcing tissue about the surgically created stoma.

11. The implantable device of claim 1, wherein said sizing pattern indicates a plurality of known diameters to which the stomal aperture can be resized.

12. An implantable device for reinforcing tissue surrounding a surgically created stoma in a patient, the device comprising:
   a graft member comprising one or more layers of a resorbable biocompatible material comprising a matrix effective to stimulate ingrowth of site-reinforcing tissue about the surgically created stoma when implanted therein,
   a stomal aperture disposed within a central portion of the graft; and
   a sizing pattern on the graft member comprising visual indicia for creating an enlarged stomal opening;
   wherein the graft member is cuttable to any of a plurality of locations along the sizing pattern to form any of a plurality of corresponding modified graft members having an enlarged stomal opening, with said modified graft members each being effective to provide reinforcement of an area generally surrounding a surgically created stoma so as to resist herniation or reherniation around the stoma.

13. The tissue-reinforcement device of claim 12, wherein the graft comprises a stomal aperture access pathway extending from the stomal aperture outward to an outer edge of the graft, the stomal aperture access pathway comprising a weakened line.

14. The tissue-reinforcement device of claim 12, wherein the sizing pattern comprises weakened lines comprising a plurality of perforations formed through material of the graft, the perforations being disposed at regular intervals from the stomal aperture, the perforations being aligned circumferentially such that they comprise indicia for determining the diameter of the resized stomal opening.

* * * * *